(12) United States Patent
Takahashi et al.

(10) Patent No.: US 6,919,443 B1
(45) Date of Patent: Jul. 19, 2005

(54) METHOD FOR ISOLATING SATELLITE SEQUENCES

(75) Inventors: Hideaki Takahashi, Tsukuba (JP); Masashi Sekino, Shiogama (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 09/762,867

(22) PCT Filed: Jul. 1, 1999

(86) PCT No.: PCT/JP99/03551

§ 371 (c)(1),
(2), (4) Date: Sep. 10, 2001

(87) PCT Pub. No.: WO00/11156

PCT Pub. Date: Mar. 2, 2000

(30) Foreign Application Priority Data

Aug. 18, 1998 (JP) .......................................... 10/232153

(51) Int. Cl.[7] ........................ C07H 21/04; C07H 21/02; C12N 15/64; C12Q 1/68
(52) U.S. Cl. .................... 536/24.2; 536/23.1; 536/24.3; 536/24.33; 435/91.4; 435/6
(58) Field of Search ............................. 536/24.2, 23.1, 536/24.3, 24.33; 435/91.4, 6, 69.1, 320.1, 455; 424/9.1

(56) References Cited

U.S. PATENT DOCUMENTS 5,047,522 A     9/1991  Nogueira et al.
5,663,319 A  *  9/1997  Bittner et al. ............... 536/24.3

OTHER PUBLICATIONS

Basler et al, Hybridization of Nuclear Matrix Attached Deoxyribonuclease Acid Fragments, Biochemistry, 1981, vol. 20, pp. 6921–6929.*

Burgtorf and Bunemann. A telomere–like satellite (GGGT-CAT)n comprises 4% of genomic DNA of *Drosophila hydei* and is located mainly in centromeric heterochromatin of all large acrocentric autosomes. Gene (1993) vol. 137, pp 287–291.*

Promega on–line catalog revised May 2000, DNA Polymerase I (Klenow) Fragment, Part# 9PIM220, copyright 1997–2000.*

Takahashi et al., "An Efficient Method to Clone Chicken Microsatellite Repeat Sequences," *Jph. Poult. Sci.*, 33:292–299 (1996).

Miki et al., "Chromosome Mapping and Gene Cloning," *Tanpakushitsu, Kakusan, Kouso, (Protein, Nucleic Acid and Enzyme)*, 41 (15):2407–2413 (1996), Japanese, no Translation.

Maniatis et al., "The Isolation of Structural Genes from Libraries of Eucaryotic DNA," *Cell*, 15:687–701 (1978).

Collection of Articles on Experiments in Biochemistry, Third Series of Nucleic Acids, Recombinant DNA Techniques, Japan Biochemical Society, Tokyo Kagaku Dozin Co., Ltd., vol. 2, §§ 2.4 and 5.4.2 (1992), English Translation May 4, 2002.

* cited by examiner

*Primary Examiner*—Gerry Leffers
*Assistant Examiner*—Maria Marvich
(74) *Attorney, Agent, or Firm*—Nixon Peabody LLP

(57) ABSTRACT

A highly homogeneous library can be obtained by cleaving a genomic DNA by a sequence-independent cleavage method, such as sonication. By selecting satellite sequences from such a library, efficiency of isolation is improved. Thus, an efficient method of isolating microsatellite sequences, which are useful as DNA markers, is provided.

1 Claim, 1 Drawing Sheet

SEQUENCE LISTING

<160> NUMBER OF SEQ ID NOS: 32

<210> SEQ ID NO 1
<211> LENGTH: 82
<212> TYPE: DNA
<213> ORGANISM: Haliotis discus discus

<400> SEQUENCE: 1
cacacacaca cacacacaca cacacacaca cacacacaca cacacacaca cacacacaca     60
cacacacaca cacacacaca ca                                              82

<210> SEQ ID NO 2
<211> LENGTH: 60
<212> TYPE: DNA
<213> ORGANISM: Haliotis discus discus

<400> SEQUENCE: 2
gactgactct cactcactca ctcactcact cactcacaca ctcacacaca cacacacaca     60

<210> SEQ ID NO 3
<211> LENGTH: 51
<212> TYPE: DNA
<213> ORGANISM: Haliotis discus discus

<400> SEQUENCE: 3

```
cccccaccc acacacacac acacacacac acatacacac acacacacac a          51

<210> SEQ ID NO 4
<211> LENGTH: 14
<212> TYPE: DNA
<213> ORGANISM: Haliotis discus discus

<400> SEQUENCE: 4
cacacacaca caca                                                  14

<210> SEQ ID NO 5
<211> LENGTH: 32
<212> TYPE: DNA
<213> ORGANISM: Haliotis discus discus

<400> SEQUENCE: 5
cacacacaca cacacacaca cacacacaca ca                              32

<210> SEQ ID NO 6
<211> LENGTH: 18
<212> TYPE: DNA
<213> ORGANISM: Haliotis discus discus

<400> SEQUENCE: 6
gagacagaca cacacaca                                              18

<210> SEQ ID NO 7
<211> LENGTH: 23
<212> TYPE: DNA
<213> ORGANISM: Haliotis discus discus

<400> SEQUENCE: 7
caaagaaccc aaacacacac aca                                        23

<210> SEQ ID NO 8
<211> LENGTH: 46
<212> TYPE: DNA
<213> ORGANISM: Haliotis discus discus

<400> SEQUENCE: 8
cgcacgcacg cacgcacgca cgcacgcacg cacgcatgca cccaca               46

<210> SEQ ID NO 9
<211> LENGTH: 25
<212> TYPE: DNA
<213> ORGANISM: Haliotis discus discus

<400> SEQUENCE: 9
ctctctcaac aacaacacac acaca                                      25

<210> SEQ ID NO 10
<211> LENGTH: 50
<212> TYPE: DNA
<213> ORGANISM: Haliotis discus discus

<400> SEQUENCE: 10
cacacacaca cacacacaca cacacacaca cacacacaca cacacacaca           50

<210> SEQ ID NO 11
<211> LENGTH: 40
<212> TYPE: DNA
<213> ORGANISM: Haliotis discus discus
```

```
<400> SEQUENCE: 11
cactcacaca cacacacaca cacacacaca cacacataca                    40

<210> SEQ ID NO 12
<211> LENGTH: 17
<212> TYPE: DNA
<213> ORGANISM: Haliotis discus discus

<400> SEQUENCE: 12
caaacacatc acacaca                                             17

<210> SEQ ID NO 13
<211> LENGTH: 60
<212> TYPE: DNA
<213> ORGANISM: Haliotis discus discus

<400> SEQUENCE: 13
cacacacaca cacacacaca cacacacaca cacacacaca cacacacaca cacacacaca    60

<210> SEQ ID NO 14
<211> LENGTH: 58
<212> TYPE: DNA
<213> ORGANISM: Haliotis discus discus

<400> SEQUENCE: 14
caagcaacca cacacacaca cacacacaca cacacacaca cacacacaca cacacaca      58

<210> SEQ ID NO 15
<211> LENGTH: 88
<212> TYPE: DNA
<213> ORGANISM: Haliotis discus discus

<400> SEQUENCE: 15
cacactcaca cacacacaca cacacacaca cacgcacgca cgcacgcacg cacgcacgca    60
cgcacgcacg cacgcacaca cacacaca                                       88

<210> SEQ ID NO 16
<211> LENGTH: 24
<212> TYPE: DNA
<213> ORGANISM: Haliotis discus discus

<400> SEQUENCE: 16
cacacacaca cacacacgcg cgcg                                     24

<210> SEQ ID NO 17
<211> LENGTH: 20
<212> TYPE: DNA
<213> ORGANISM: Haliotis discus discus

<400> SEQUENCE: 17
cacacacaca cacgcgcgcg                                          20

<210> SEQ ID NO 18
<211> LENGTH: 10
<212> TYPE: DNA
<213> ORGANISM: Haliotis discus discus

<400> SEQUENCE: 18
cacacacaca                                                     10

<210> SEQ ID NO 19
<211> LENGTH: 52
```

-continued

<212> TYPE: DNA
<213> ORGANISM: Haliotis discus discus

<400> SEQUENCE: 19
cacacacaca cacacacaca cacacacaca cacacacaca cacacacaca ca        52

<210> SEQ ID NO 20
<211> LENGTH: 30
<212> TYPE: DNA
<213> ORGANISM: Haliotis discus discus

<400> SEQUENCE: 20
tacatacaca cacacacaca cacacacaca                                  30

<210> SEQ ID NO 21
<211> LENGTH: 20
<212> TYPE: DNA
<213> ORGANISM: Haliotis discus discus

<400> SEQUENCE: 21
cacacaaaca cacacacaca                                             20

<210> SEQ ID NO 22
<211> LENGTH: 30
<212> TYPE: DNA
<213> ORGANISM: Haliotis discus discus

<400> SEQUENCE: 22
cacaaccaca caaccaccac cacacacaca                                  30

<210> SEQ ID NO 23
<211> LENGTH: 24
<212> TYPE: DNA
<213> ORGANISM: Haliotis discus discus

<400> SEQUENCE: 23
cacacacaca cacacatgca tgca                                        24

<210> SEQ ID NO 24
<211> LENGTH: 68
<212> TYPE: DNA
<213> ORGANISM: Haliotis discus discus

<400> SEQUENCE: 24
cacacacaca cacacacaca cacacacaca cacacacaca cacacacaca cacacacaca  60
cacacaca                                                          68

<210> SEQ ID NO 25
<211> LENGTH: 44
<212> TYPE: DNA
<213> ORGANISM: Haliotis discus discus

<400> SEQUENCE: 25
cacacacaca cacgcacg cacgaacgca cgcaaacaca cgcg                    44

<210> SEQ ID NO 26
<211> LENGTH: 16
<212> TYPE: DNA
<213> ORGANISM: Haliotis discus discus

<400> SEQUENCE: 26
cacacacaca cacaca                                                 16

```
<210> SEQ ID NO 27
<211> LENGTH: 32
<212> TYPE: DNA
<213> ORGANISM: Haliotis discus discus

<400> SEQUENCE: 27
cacccccccc cacacacaca cacacacacc cc                           32

<210> SEQ ID NO 28
<211> LENGTH: 16
<212> TYPE: DNA
<213> ORGANISM: Haliotis discus discus

<400> SEQUENCE: 28
cacacacaca cagaga                                             16

<210> SEQ ID NO 29
<211> LENGTH: 52
<212> TYPE: DNA
<213> ORGANISM: Haliotis discus discus

<400> SEQUENCE: 29
cacacacaca cacacacaca cacacacaca cacacacaca cacacacaca ca     52

<210> SEQ ID NO 30
<211> LENGTH: 50
<212> TYPE: DNA
<213> ORGANISM: Haliotis discus discus

<400> SEQUENCE: 30
cacacacaca cacacacaca cacacacaca cacacacaca cacacacaca        50

<210> SEQ ID NO 31
<211> LENGTH: 17
<212> TYPE: DNA
<213> ORGANISM: Haliotis discus discus

<400> SEQUENCE: 31
cagcacacac acataca                                            17

<210> SEQ ID NO 32
<211> LENGTH: 61
<212> TYPE: DNA
<213> ORGANISM: Haliotis discus discus

<400> SEQUENCE: 32
caaacaaaca aacacacaca caaacacaca cacacacaca cacacacagg cacggcggcg   60
g                                                                  61
```

US 6,919,443 B1

METHOD FOR ISOLATING SATELLITE SEQUENCES

TECHNICAL FIELD

The present invention relates to a method for isolating satellite sequences. Satellite sequences, which are useful as population genetic markers, can be used as markers for genetic linkage analyses, etc. Therefore, an efficient technique for isolating them is an important subject of research in the field of genome analysis.

BACKGROUND ART

It has been known that eukaryotic genomes contain repetitive sequences consisting of similar nucleotide sequence repeats. The first discovered repetitive sequence had a repeat unit consisting of satellite DNA, which is a long sequence ranging from several hundred to several thousand bases, and is called a satellite sequence (Bioscience, 27: 790–796, 1977). Repetitive sequences consisting of shorter nucleotide sequence units were later identified. They have been named, depending on the size of their repeat unit, microsatellite sequences (Am. J. Hum. Genet., 4: 397–401, 1989) when they have a repeat unit of 2 to 5 bases (Nucleic Acids Res. 9: 5931–5947, 1981) or minisatellite sequences (Nature, 314: 67–73, 1985) when they have a repeat unit of 10 to 64 bases (Nature, 295: 31–35, 1982). Microsatellite sequences are also called simple sequences (Nucleic Acids Res. 17: 6463–6471, 1989) or short tandem repeats (Am. J. Hum. Genet. 49: 746–756), etc.

Use of microsatellite sequences as markers was not reported when they were discovered. However, after their polymorphism was confirmed by polymerase chain reaction (PCR) (Am. J. Hum. Genet. 4: 397–401, 1989), they have attracted the attention of researchers for their use as markers in a variety of areas. Specifically, their application to pedigree or lineage discrimination and individual identification of humans, animals, and plants is known. Because microsatellite sequences are scattered throughout a genome and abound in variation, they are good genetic markers. Furthermore, a microsatellite DNA polymorphism contains many polymorphic gene loci and a large number of alleles per gene locus. In addition, based on PCR, microsatellite DNA polymorphism analysis is easy to perform. The amplified products are easily detected as single or double bands by electrophoresis, which simplifies determination of individual types and facilitates the data processing. Therefore, microsatellite DNA markers have become widely used as the most effective markers for population genetics (J. Fish. Biol., 47: 29–55, 1995).

For microsatellite DNA polymorphism analysis, first, a variety of microsatellite DNA should be isolated from individual species to be analyzed. In addition, the microsatellite DNA regions should be amplified by PCR to detect the microsatellite polymorphism. Appropriate primers are needed for PCR. This means that, to perform microsatellite DNA polymorphism analysis, efficient methods for isolating microsatellite DNA from the species and for designing PCR primers capable of amplifying the microsatellite region are required.

The inventors have already reported a method that is expected to allow efficient isolation of microsatellites from poultry, for which microsatellite polymorphism analysis is not advanced (Jpn. Poult. Sci., 33: 292–299, 1996). This method is an improvement on a conventional method of microsatellite sequence isolation that consists of a series of manipulations: fragmentation of a genome with restriction enzymes, insertion of the fragments into a vector, extension reaction with $(TG)_n$ primers, and then cloning (Proc. Natl. Acad. Sci. USA 89: 3419–3423, 1992). Namely, isolation of unknown microsatellite sequences was achieved by choosing a vector with high transformation efficiencies, by specifically digesting single-stranded DNA with mung bean nuclease, or by removing bacterial DNA and RNA with DNase I and RNase A. In chicken, it is considered difficult to efficiently isolate microsatellite sequences, because the number of microsatellite sequences is small. The above method could achieve, by calculation, six times more efficient isolation than the known method that was used in an attempt to isolate chicken microsatellite sequences (Poultry Science, 74: 1855–1874, 1995).

However, even by this method, it was impossible to prevent problematic clones from contaminating the microsatellite DNA clones obtained. Namely, a high rate of duplicate clones was found among the clones obtained, suggesting bias in the constitution of clones as well as low efficiency.

Microsatellite sequences are required to be isolated according to each species. There are few species for which the isolation of microsatellite sequences is in progress, and it is still necessary to isolate microsatellile sequences from many species. However, there are a number of species-specific problems, for example, low frequency of microsatellite sequences in the chicken genome. Therefore, it is useful to provide a novel technique for isolating microsatellite sequences, also because it will enable selection from a variety of approaches.

DISCLOSURE OF THE INVENTION

An objective of the present invention is to provide a method for isolating satellite sequences with high isolation efficiency. The present invention provides an isolation method more efficient than any known technique.

The present inventors presumed that one of the major causes for generating duplicate clones during isolation of satellite sequences by known techniques might come from the fragmentation of the genomic DNA. In other words, the possibility that, when digested with restriction enzymes, the genomic library is biased due to the fact that sequence-specific cleavage cannot be excluded.

Therefore, the inventors attempted to utilize a nucleotide sequence-independent cleavage method in which more arbitrary cleavage of the genomic DNA is expected. As a result, they found that cleavage of genomic DNA is possible with nucleotide sequence-independent DNA-digesting enzymes or by a physical action. However, since most of the physically cleaved genomic DNA fragments are not phosphorylated at their ends, they are not allowed to be efficiently incorporated into vectors using an enzyme. In addition, since physically cleaved fragments have an irregularly protruding strand at their cleavage site, they cannot be ligated. The inventors have overcome these problems by using several enzymatic treatments, and have established a method to obtain a more homogeneous genomic library. Furthermore, they have confirmed that the library thus obtained enables efficient isolation of satellite sequences, thereby completing the present invention. As used herein, the term "satellite sequences" indicates, unless otherwise mentioned, any repeat sequences which include microsatellite sequences and minisatellite sequences. Also as used herein, "microsatellite sequences" and "minisatellite sequences" indicate repeat sequences consisting of repeat units of 2 to 5 bp and 10 to 64 bp, respectively. Thus, the present invention relates to the following methods for isolating satellite sequences.
(1) An isolation method for satellite sequences, wherein a genomic DNA is cleaved by a nucleotide sequence-independent method, the isolation method comprising:
a) obtaining randomly cleaved fragments of the genomic DNA and
b) selecting, from the fragments obtained in a), fragments comprising the satellite sequences.
(2) The isolation method of (1), wherein the nucleotide sequence-independent method is a physical cleavage method or an enzymatic cleavage method.
(3) The isolation method of (2), wherein the physical cleavage method is sonication.
(4) The isolation method of (3), wherein the ends of the genomic DNA that have been fragmented by sonication are to be blunted.
(5) The isolation method of (4), wherein the ends are to be blunted with DNA polymerase having single strand-specific endonuclease activity and 3'→5' exonuclease activity.
(6) The isolation method of (2), wherein a nucleotide sequence-independent endonuclease is used in the enzymatic cleavage method.
(7) The isolation method of (6), wherein the nucleotide sequence-independent endonuclease is DNase I.
(8) The isolation method of (1), wherein the satellite sequences are microsatellite sequences.
(9) Use of satellite sequences isolated by the isolation method of any one of (1) to (8) as DNA markers.

In the present invention, it is critical to cleave a genomic DNA using a nucleotide sequence-independent cleavage method that gives random fragments. Cleavage of a genomic DNA using a nucleotide sequence-independent cleavage method refers to cleaving DNA without dependence on structural characteristics (i.e., nucleotide sequences) of the DNA. Therefore, neither chemical reactions in which DNA is cleaved in a nucleotide sequence-dependent manner nor digestion with restriction enzymes constitutes the cleavage method of the present invention. The genomic DNA to which the method of the present invention is to be applied can be prepared by known methods. Namely, cells are lysed enzymatically with protease, and are subjected to DNA extraction using an appropriate solvent.

For cleavage of a genomic DNA using a nucleotide sequence-independent cleavage method, any of the above-described cleavage methods, for example, those based on physical actions and those based on the action of DNA-digesting enzymes that do not recognize the nucleotide sequence, can be used. Physical actions include sonication and agitation. On the other hand, as DNA-digesting enzymes that do not recognize the nucleotide sequence, DNase I and the like are known. Any of these methods can be used in the present invention. Above all, treatment by sonication is one of the most desirable manipulations with excellent reproducibility. By sonication, a large quantity of fragments with uniform lengths can be obtained in a short time. In contrast, partial digestion of a genomic DNA with DNase I requires strict setting of conditions for reproducibly obtaining fragments with uniform lengths. In addition, this method often requires troublesome manipulations.

As to the extent of cleavage of a genomic DNA, those skilled in the art can empirically set the conditions that will permit efficient production of fragments having the optimal size for the satellite sequence of interest. For example, if isolation of microsatellite sequences is intended, such conditions that give a library of fragments of 300 to 900 bp are selected. Considering the operation of ligating the cleaved fragments into a vector, it is desirable to use conditions under which the majority of fragments generated have a size of 300 to 500 bp or 500 to 800 bp. This is because, if fragments contain integral multiples of smaller fragments, such fragments are indistinguishable from the ligated products of more than one smaller fragment. For instance, when sonication at 20 kHz with an amplitude of 10 is performed on ice, fragments of 300 to 500 bp can be efficiently obtained if a sonication of 1-minute duration is performed 1 to 5 times. Since a prolonged sonication may heat the sample and denature DNA, it is desirable to repeat the sonication with a shorter time duration.

The genomic DNA cleaved by physical actions such as sonication tends to exhibit poor ligation efficiency, which prevents efficient incorporation of the DNA into vectors. For this reason, it is desirable to blunt the ends of the DNA fragments. In the present invention, any of the known blunting methods can be used: removal of the protruding ends with single strand-specific endonuclease, and further synthesis of the complementary strand at the 3' recessed ends with DNA polymerase to ensure the blunting. Specifically, mung bean nuclease and S1 nuclease can be used as the single strand-specific endonucleases. On the other hand, DNA polymerase having 3'→5' exonuclease activity can be used as the DNA polymerase. Such DNA polymerases include T4 DNA polymerase, pfu polymerase, and KOD polymerase. Mung bean nuclease, which is used in the Example, is a single strand-specific endonuclease and achieves blunting by digesting the protruding portion of the single strands of the DNA. In the Example, the action of T4 DNA polymerase is further utilized to ensure the blunting. T4 DNA polymerase digests the protrusion at the 3' ends by its strong 3—→5' exonuclease activity, and at the same time, it can synthesize complementary strands at the 3' recessed ends, thereby giving blunt ends. However, T4 DNA polymerase cannot blunt a recessed 3' end with a phosphate group. Therefore, it is desirable to use mung bean nuclease and T4 DNA polymerase together. In such a case, treatment with mung bean nuclease cleaves gaps generated in the double-stranded DNA by sonication, as well as blunts the ends. As a result, fragments with lengths shorter than expected may be produced. In order to obtain a library free from shorter fragments, it is desirable to provide a step of isolating the fragments of expected size after treating with mung bean nuclease. Fragments of expected sizes can be isolated by agarose gel electrophoresis or by gel filtration. The blunt-ended genomic DNA fragments can be directly ligated into vectors. Alternatively, they can be phosphorylated at their 5' ends to improve the efficiency of ligation. T4 polynucleotide kinase can be used for phosphorylation.

The genomic DNA fragments with phosphorylated 5' ends can self-ligate during the ligation into the vector. To prevent the self-ligation, the concentration of the fragments should be reduced, while excess concentration of the vector is employed so as to increase the opportunities for the fragments to be ligated into the vector. For the ligation reaction, T4 DNA ligase works in the ligation buffer and ligation efficiency can be further improved by carrying out the ligation in the presence of the restriction enzyme used to cleave the vector. For example, when pCR-ScriptSK(+) is used as the vector, restriction enzyme SrfI can help keep the vector in a linear state. Since SrfI does not act on the vector into which an insert is ligated, one can expect the ligation efficiency to be improved.

In the present invention, not only physical actions but also nucleotide sequence-independent DNA-digesting enzymes can be used for fragmentation of DNA. These enzymes include, for example, DNase I, etc. For enzymatic treatment with DNase I, conditions that allow uniform action of the enzyme on the whole genome and that also allow production of fragments with expected sizes should be empirically provided. For example, in order to maintain the enzymatic action in a uniform state, genomic DNA with highest purity should be used after nuclear proteins are removed. Also, the enzymatic reaction should be performed as quickly as possible in order to avoid producing a large number of small fragments. In addition, conditions such as reaction time and temperature should be accurately controlled in order to maintain high reproducibility. After the enzymatic reaction is completed, the reaction is stopped by heating or other means. The nucleic acid component is recovered from the reaction, and, if necessary, particular fragments are extracted, followed by incorporation of the fragments. into the vectors as described above. The fragments of the genomic DNA digested with the enzyme are blunt-ended and phosphorylated, which allows them to be directly used for ligation.

The vectors used in the present invention are not specially restricted. Specifically, known vectors such as pCR-ScriptSK(+), pBluescriptKS(+) (both are manufactured by Stratagene), and pUC18 can be used. After an appropriate host is transformed with the vector including the insert and is grown, the DNA is recovered to make a genomic library. When pCR-ScriptSK(+) is used for transformation, it may be advantageous to use host strains having excellent transformation efficiencies, such as *E. coli* (competent cell) XL1-Blue MRF', XL2-Blue MRF', and TG1 (all are manufactured by Stratagene).

Using the genomic library thus constructed, transformants containing the satellite sequences of interest can be cloned. Screening for the satellite sequences can be performed based on colony hybridization using a probe for a satellite sequence (Can. J. Fish. Biol. 51: 1959–1996, 1994) or on primer extension (Proc. Natl. Acad. Sci. USA, 89: 3419–3423, 1992). In colony hybridization, colonies of the transformed cells as described above are transferred onto a filter, and hybridized with a probe having, for example, a repeat sequence of $(GT)_n$. The nucleotide sequence of the oligonucleotide that constitutes the probe is properly provided based on the satellite sequence of interest. Positive colonies are separated to isolate the clones containing the satellite sequence.

In primer extension, on the other hand, the genomic library is recovered as single-stranded DNA. For example, if pCR-ScriptSK(+) is used as the vector, the transformed *E. coli* cells can be infected with helper phage VCS-M13 or the like to recover the inserts in a single-stranded form as recombinant phages. Since DNA packaged in the phage is protected against enzymatic action, RNA and DNA derived from *E. coli* can be enzymatically degraded when the DNA of interest is recovered, thereby achieving more efficient cloning.

To the single-stranded plasmid DNA isolated from the phage, a primer specific to the satellite sequence is annealed, and then, DNA polymerase is applied. For example, repetitive sequences of $(dA-dT)_n$ are generally (0.3% of the entire genomic DNA) found in the mammalian microsatellite sequences. In humans, such combinations as $(dC-dA/dT-dG)_n$ and $(dC-dT/dA-dG)_n$ are also frequently observed. Based on such information, one can design primers that comprise a nucleotide sequence complementary to a satellite sequence and that anneal to the satellite sequence. It is advantageous to phosphorylate the 5' end of the primer beforehand. Vectors that contain a microsatellite sequence acquire the primer at this site and a double-stranded DNA is synthesized, while those to which the primer does not anneal remain single-stranded. Ligation is performed after the synthesis of the complementary strand with DNA polymerase to complete the double-stranded circular DNA, and then the single-stranded DNA is digested with mung bean nuclease or the like. Consequently, only the vectors containing the satellite sequences remain. These vectors can be recovered and used to transform cells, thereby cloning the vectors. After amplifying the cloned vectors containing the satellite sequences, one can recover the DNA and determine the sequences, thereby completing the isolation of the satellite sequences.

When a satellite sequence is isolated together with its flanking regions, primers for PCR can be designed. For designing the primers, it is convenient to utilize a commercially available package of software for sequence analysis. For example, in the Example below, a primer designing software Primer Premier (Premier Biosoft International) is used. The microsatellite sequences and minisatellite sequences isolated are useful as fingerprint markers for intraspecies analysis or as pedigree (or lineage) markers. If any satellite sequence obtained in the present invention exhibits a polymorphism, such a nucleotide sequence can be used as an indicator for identification of individuals. Such a satellite sequence is called a fingerprint marker. Since satellite sequences used as fingerprint markers are inherited from the parents of an individual, analysis of the fingerprint markers conserved among multiple individuals indicates the probability that these individuals belong to a single pedigree. Such use of a satellite sequence is called a pedigree (or lineage) marker.

Furthermore, the satellite sequences isolated in the present invention can also be used as genetic linkage markers, in addition to the use as fingerprint markers and pedigree (or lineage) markers. In the present invention, a satellite marker utilized as an indicator represented by the uses exemplified above is called a DNA marker.

BEST MODE FOR CARRYING OUT THE INVENTION

Figure 1:
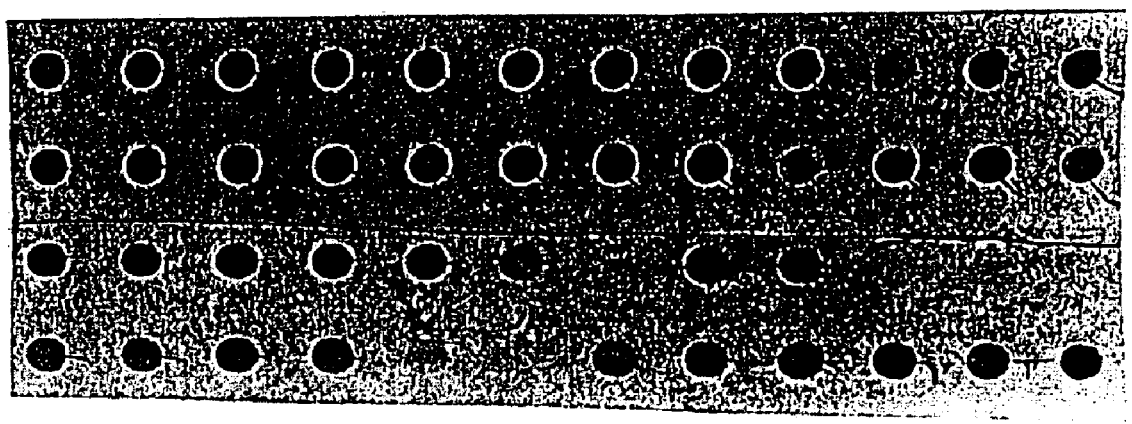
FIG. 1 shows the image of a dot-blot assay with a microsatellite sequence-specific probe ($(CA)_{10}$ oligonucleotide).

The present invention is described more specifically in the following examples.

(1) Preparation of DNA Fragments from Black Abalone

Black abalone (Haliotis discus discus) DNA was isolated from foot muscle according to the TNES-Urea method (Fisheries Sci., 62: 723–726, 1996). However, 4 M urea was used herein. The genomic DNA solution (20 $\mu$g/ml, 550 $\mu$l) was sonicated (20 kHz, Amplitude 10, for one minute, five times) with cooling to fragment the DNA. A reaction mixture (52 $\mu$l) containing the substrate DNA (about 10 $\mu$g), 30 mM $CH_3COONa$ (pH 4.6), 50 mM NaCl, 1 mM $(CH_3COO)_2$ Zn, 5% glycerol, and 60 units of mung bean nuclease (Toyobo) was incubated for 1 hour at 37° C. to cleave the gap portions of the DNA fragments and to blunt the protruding ends. By electrophoresis on a 1.2% agarose gel, DNA fragments of 300 to 500 bp were recovered. A reaction mixture (100 $\mu$l) containing the recovered substrate DNA, 20 $\mu$M dNTP, 50 mM Tris/HCl (pH 8.5), 7 mM $MgCl_2$, 15 mM $(NH_4)_2SO_4$, 10 mM 2-mercaptoethanol, 0.1 mM EDTA, and 10 units of T4 DNA polymerase (Toyobo) was incubated for 1 hour at 37° C. to blunt the protruding ends of the DNA fragments. Further, a reaction mixture (50 µl) containing the substrate DNA, 0.2 mM rATP, 50 mM Tris/HCl (pH 7.6), 10 mM $MgCl_2$, 10 mM 2-mercaptoethanol, and 10 units of T4 polynucleotide kinase (Toyobo) was incubated for 1 hour at 37° C. to phosphorylate the 5' ends of the DNA fragments.

(2) Ligation of Genomic DNA Fragments into Plasmid Vectors

A reaction mixture (10 µl) containing pCR-Script SK(+) vector (Stratagene) (about 1 µl), 25 mM Tris/Acetate (pH 7.6), 100 mM KOAc, 10 mM MgOAc, 0.5 mM 2-mercaptoethanol, 10 µl/ml BSA, and 10 units of restriction enzyme SrfI (Stratagene) was incubated for 1 hour or more at 37° C., to cleave the vector at the SrfI site. A reaction mixture (50 µl) containing the vector solution prepared, the substrate DNA (about 3 µg), 10 units of SrfI, 0.5 mM rATP, 66 mM Tris/HCl (pH 7.6), 6.6 mM $MgCl_2$, 10 mM dithiothreitol, and 20 units of T4 DNA ligase (Toyobo) was incubated overnight at 24° C. to ligate the DNA fragments into the vector. After inactivating the DNA ligase by heating at 65° C. for 15 minutes, 10 units of SrfI was further added. The reaction mixture was incubated for 1 hour at 37° C. to digest the self-ligated vector.

(3) Preparation of Single-Stranded DNA

To each of five culturing tubes, 100 µl of XL2-Blue MRF' ultracompetent cells (*Epicurian coli* ultracompetent cells; Stratagene) was added, and then, the ligated vector (about 200 ng) was added, followed by transformation according to the attached instruction manual. After 900 µl of NZY medium (Maniatis, Molecular Cloning: A Laboratory Manual, 2nd ed., Cold Spring Harbor Laboratory Press, New York, 1989) was added to each of the tubes, the cells were cultured for one hour at 37° C. with shaking. Subsequently, ampicillin was added to a final concentration of 50 µg/ml. The cells were cultured for another hour at 37° C. with shaking to select the transformed *E. coli*. To each of the tubes, about $10^{10}$ pfu of VCS-M13 helper phage was added. The cells were allowed to stand for 20 minutes at 37° C., followed by addition of kanamycin at a final concentration of 70 µg/ml. The cells were cultured for 1 hour at 37° C. with shaking to select the *E. coli* infected with the helper phage. All the cultures were put together and added to 100 ml of Terrific medium (Maniatis, Molecular Cloning: A Laboratory Manual, 2nd ed., Cold Spring Harbor Laboratory Press, New York, 1989) containing ampicillin and kanamycin. The cells were cultured for 14 hours at 37° C. with shaking. The Terrific medium was centrifuged at 14,000 rpm for 10 minutes at 0° C., and the supernatant was recovered and filtered twice through a 45 µm filter. After precipitating twice with PEG according to the standard method (Muramatsu, Lab Manual of Genetic Engineering, 3rd ed., Maruzen, Tokyo, 1996, pp.51–55), the DNA and RNA derived from *E. coli* were digested according to a known method (Jpn. Poult. Sci. 33: 292–299, 1996). Subsequently, PEG precipitation, phenol extraction, and ethanol precipitation were performed to purify the single-stranded DNA.

(4) Selection of $(CA)_n$-Positive Plasmids

Primer extension was performed using a $(CA)_{12}$ oligonucleotide to select the plasmid DNA into which DNA fragments with (TG/CA) repeats had been inserted. The solution (98 µl) containing the single-stranded DNA (about 3 µg), 0.2 mM dNTP, 20 mM Tris/HCl (pH 8.8), 10 mM KCl, 10 mM $)_2SO_4$, 2 mM $MgSO_4$, 100 µg/ml BSA, 0.1% Triton X-100, and 100 pmol $(CA)_{12}$ oligonucleotide was pre-heated at 72° C. for 10 minutes. Five units of Pfu DNA polymerase (Stratagene) was added to the solution, which was then overlaid with mineral oil and incubated for 30 minutes at 72° C. Subsequently, the generated double-stranded DNA was recovered by phenol extraction and ethanol precipitation and was dissolved in 10 µl of sterilized water. After circularizing the double-stranded DNA by using a ligation kit (Ligation high, Toyobo), the DNA ligase was inactivated by heat treatment (65° C. for 15 minutes). A reaction mixture (100 µl) containing this solution, 30 mM $CH_3COONa$ (pH 4.6), 50 mM NaCl, 1 mM $(CH_3COO)_2Zn$, 5% glycerol, and 30 units of mung bean nuclease (Toyobo) was incubated for 2 hours or more at 37° C. to digest the single-stranded DNA which had not been primer-extended. DNA was recovered by phenol/chloroform extraction and ethanol precipitation, and was dissolved in 60 µl of TE buffer.

With the recovered DNA (equivalent to 100 µg of the single-stranded DNA), XL2-Blue MRF' Ultracompetent cells were transformed. The transformed cells were spread onto a 2×YT agar medium containing 50 µg/ml ampicillin (Maniatis, Molecular Cloning: A Laboratory Manual, 2nd ed., Cold Spring Harbor Laboratory Press, New York, 1989), and cultured overnight at 37° C. Single colonies on the culture plate were picked up at random, and cultured overnight at 37° C. with shaking in 2 ml of 2×YT medium (Maniatis, Molecular Cloning: A Laboratory Manual, 2nd ed., Cold Spring Harbor Laboratory Press, New York, 1989) containing ampicillin at a final concentration of 50 µg/ml. The plasmid was extracted by the alkaline method according to the standard procedure (Muramatsu, Lab Manual of Genetic Engineering, 3rd ed., Maruzen, Tokyo, 1996, pp.51–55), and dissolved in 50 µl of TE buffer.

The purified plasmid DNA (equivalent to 4 ng of the single-stranded DNA) was alkaline-denatured with 0.5 N NaOH and blotted onto a nylon membrane (No. 1209299, Boehringer Mannheim). The membrane was baked at 120° C. for 30 minutes. Using $(CA)_{10}$ oligonucleotide digoxigenin-labeled with the DIG oligonucleotide labeling kit (DIG Oligonucleotide Tailing Kit, Boehringer Mannheim) as a probe, and using the DIG nucleic acid detection kit (DIG Nucleic Acid Detection Kit, Boehringer Mannheim), $(CA)_n$-positive plasmids were detected according to the manufacturer's instruction. Part of the results is shown in FIG. 1.

(5) Cycle Sequencing

For the $(CA)_n$-positive clones, nucleotide sequences were determined using the cycle sequencing method. A KS primer labeled with Cy5 at its 5' end, a Reverse primer, and a sequencing kit (ThermoSequence fluorescent labeled primer cycle sequencing kit with 7-deaza-dGPT; Amersham) were used for the sequencing reaction. The fluorescent DNA sequencer (ALFexpress, Pharmacia) was used for sequencing. Based on the nucleotide sequence data thus obtained, optimal primers were designed for the region encompassing the CA repeats using software for primer design (Primer Premier; Premier Biosoft International). The nucleotide sequences of the microsatellite sequences isolated from the black abalone are shown below. Repetitive units are shown in the parentheses so that they are easily recognized. The actual sequences are as shown in the sequence listing (the numbers correspond to the SEQ ID NOs). For the regions 1 to 24, PCR primers can be designed, and a polymorphism was identified for nine regions (1, 3, 8, 10, 13, 15, 16, 19, and 24).

1. $(CA)_{41}$
2. $(GACT)_2(CTCA)_7(CA)_2CT(CA)_9$
3. $C_5CAC_2(CA)_{12}TA(CA)_8$

4. $(CA)_7$
5. $(CA)_{16}$
6. $(GA)_2CAGA(CA)_5$
7. $CA_3GA_2C_3A_3(CA)_5$
8. $(CGCA)_9TGCAC_2(CA)_2$
9. $(CT)_3(CA_2)_3(CA)_5$
10. $(CA)_{25}$
11. $CACT(CA)_{16}TACA$
12. $CA_3(CA)_2T(CA)_4$
13. $(CA)_{30}$
14. $CA_2GCA_2C(CA)_{25}$
15. $(CA)_2CT(CA)_{13}(CGCA)_{11}(CA)_6$
16. $(CA)_8(CG)_4$
17. $(CA)_6(CG)_4$
18. $(CA)_5$
19. $(CA)_{26}$
20. $TACATA(CA)_{12}$
21. $(CA)_2CA_3(CA)_6$
22. $(CA)_2AC(CA)_3AC(CAC)_2(CA)_5$
23. $(CA)_8(TGCA)_2$
24. $(CA)_{34}$
25. $(CA)_7(CGCA)_2CGA_2(CGCA)_2A_2(CA)_2(CG)_2$
26. $(CA)_8$
27. $CAC_8(CA)_9C_4$
28. $(CA)_6(GA)_2$
29. $(CA)_{26}$
30. $(CA)_{25}$
31. $CAG(CA)_5TACA$
32. $(CA_3)_3(CA)_4CA_3(CA)_{12}G_2CA(CG_2)_3$

About 85% (41 clones) of the $(TG/CA)_n$-concentrated library constructed based on the sequence-independent cleavage method using sonication was found to be $(CA)_n$-positive clones (FIG. 1). Out of them, 32 $(CA)_n$-positive clones were selected at random and sequenced. As a result, PCR primers were designed for 24 clones (72%). For the rest of the clones (9 clones), it was impossible to design the primers because some repeat regions were adjacent to the ligation site on the vector, because some regions were ligated into the vector in the middle of the repeat, or because some repeats were scattered throughout the DNA fragment.

INDUSTRIAL APPLICABILITY

The present invention makes it possible to efficiently isolate satellite sequences such as microsatellite sequences. Since the present invention utilizes a sequence-independent cleavage method for fragmentation of a genomic DNA, it is not influenced by the nucleotide sequence, and enables the production of unbiased libraries. Satellite sequences isolated from the unbiased library contain reduced redundancy. Thus, the present invention enables efficient isolation of satellite sequences.

For instance, the present inventors have succeeded in obtaining a $(TG/CA)_n$-concentrated library comprising 32 clones by a single manipulation from black abalone, a source from which no microsatellite sequences have been isolated previously. The clones obtained from this library are free from redundancy. It can be concluded that, compared with the previous method that produced many duplicated clones for chicken, the present method has increased the efficiency of the isolation. The isolated clones can serve for designing PCR primers as well as show reduced sequence redundancy, which is another striking effect of the present invention. For instance, calculated from the result of the example, at least 60% (0.85×24/32) of the clones cultured on the plate can be used to design PCR primers. These results reveal that the methods of the present invention for isolating microsatellite sequences are excellent methods that can be widely applied.

Furthermore, the satellite sequences isolated by the methods of the present invention can be utilized as DNA markers, such as fingerprint markers, pedigree (or lineage) markers, and genetic linkage markers.

What is claimed is:

1. An isolation method for microsatellite sequences, wherein a genomic DNA is cleaved by an enzymatic cleavage method, the isolation method comprising:
   a) producing randomly cleaved fragments of the genomic DNA using DNAse I, wherein the fragments have blunt-ends,
   b) incorporating the fragments into appropriate vectors, and
   c) selecting, from the fragments, fragments comprising microsatellite sequences.

* * * * *